United States Patent
Lacy

(10) Patent No.: US 9,341,308 B2
(45) Date of Patent: May 17, 2016

(54) POLE CLAMP

(71) Applicant: SMITHS MEDICAL ASD, INC., Rockland, MA (US)

(72) Inventor: Christopher Allen Lacy, Arden Hills, MN (US)

(73) Assignee: SMITH MEDICAL ASD, INC., Rockland, MA (US)

( * ) Notice: Subject to any disclaimer, the term of this patent is extended or adjusted under 35 U.S.C. 154(b) by 0 days.

(21) Appl. No.: 14/595,521

(22) Filed: Jan. 13, 2015

(65) Prior Publication Data

US 2015/0198283 A1  Jul. 16, 2015

Related U.S. Application Data

(60) Provisional application No. 61/927,252, filed on Jan. 14, 2014.

(51) Int. Cl.
| | |
|---|---|
| *F16B 2/02* | (2006.01) |
| *F16M 13/02* | (2006.01) |
| *A61B 19/00* | (2006.01) |
| *E05B 73/00* | (2006.01) |

(52) U.S. Cl.
CPC .............. *F16M 13/022* (2013.01); *A61B 19/00* (2013.01); *E05B 73/0082* (2013.01); *A61B 2019/267* (2013.01); *F16M 2200/02* (2013.01)

(58) Field of Classification Search
CPC .............. F16B 2/02; F16B 2/065; F16B 2/14; A61M 5/1415; F16L 3/18
USPC ......... 248/55, 227.3, 231.71, 229.15, 229.25, 248/230.8; 269/143
See application file for complete search history.

(56) References Cited

U.S. PATENT DOCUMENTS

| | | | | |
|---|---|---|---|---|
| 2,423,933 A | * | 7/1947 | Gosh ....................... | A01K 97/10 |
| | | | | 248/231.71 |
| 3,448,957 A | * | 6/1969 | Friedman ............... | A45D 44/14 |
| | | | | 223/66 |

(Continued)

FOREIGN PATENT DOCUMENTS

| | | |
|---|---|---|
| GB | 581429 | 10/1946 |
| JP | 2007-125248 A | 5/2007 |
| KR | 10-2013-0114533 A | 10/2013 |

OTHER PUBLICATIONS

Medline, I.V. Pole Stands and Tool-Free Accessories as available at https://www.medline.com/irj/servlet/prt/portal/prtroot/pcd!3aportal_content!2fmedline!2fGlobal!2fPublicDocs/publicdocuments/Medline%20Documents/Marketing%20Materials/MarketingDocuments_AI/IV%20PolesSell%20sheet%20MKT209237_LIT094R.pdf, © 2010, 4 pages.

(Continued)

*Primary Examiner* — Cassandra Davis
(74) *Attorney, Agent, or Firm* — Patterson Thuente Pedersen, P.A.

(57) ABSTRACT

A pole clamp for mounting a medical device to a pole. The pole clamp includes a main body, including a first portion including a threaded hole therethrough, a second portion that is disposed at an angle relative to the first portion, and a pivot post disposed in the second portion. A threaded adjustment rod is rotatably disposed in and through the threaded hole of the first portion. The threaded adjustment rod has a knob at a first end thereof and a push plate at a second end thereof. A rotatable stop block has a plurality of faces and is rotatably coupled to the pivot post. The rotatable stop block is rotatable to a plurality of positions to align a selected one of the plurality of faces opposite the push plate.

7 Claims, 8 Drawing Sheets

(56) References Cited

U.S. PATENT DOCUMENTS

| | | | |
|---|---|---|---|
| 4,832,299 A | | 5/1989 | Gorton |
| 4,844,397 A | | 7/1989 | Skakoon |
| 5,169,106 A | | 12/1992 | Rasmussen |
| 5,230,496 A | | 7/1993 | Shillington |
| 5,779,207 A | | 7/1998 | Danby |
| 5,836,559 A | | 11/1998 | Ronci |
| 5,918,843 A | * | 7/1999 | Stammers ............... E04G 5/04 108/28 |
| 8,011,629 B2 | | 9/2011 | Herskovic |
| 8,695,957 B2 | * | 4/2014 | Quintania ............... B25B 5/006 248/309.1 |
| 2010/0258690 A1 | | 10/2010 | Kleitsch |
| 2010/0314517 A1 | | 12/2010 | Patzer |

OTHER PUBLICATIONS

Farley, WT, IV Poles & Stands, available at https://www.wtfarley.com/iv-poles, as of Jun. 2, 2015, © 2015, 2 pages.

SENSITEC Sensitive Technology, IV Poles and IV-stands systems, available at http://www.sensitec.nl/index.php?id=65, © 2006-2007, 1 page.

Centicare Corporation, "The Finest IV Poles in the Healthcare Industry", as available at http://wvvw.centicare.com/Brochure_IV_Poles.pdf, as of Jun. 2, 2015, 12 pages.

International Search Report and Written Opinion, International Application No. PCT/US2015/011134, mailed Apr. 29, 2015, 5 pages.

Application and File History for U.S. Appl. No. 12/457,510, filed Jun. 12, 2009, Inventor: Charles R. Patzer.

* cited by examiner

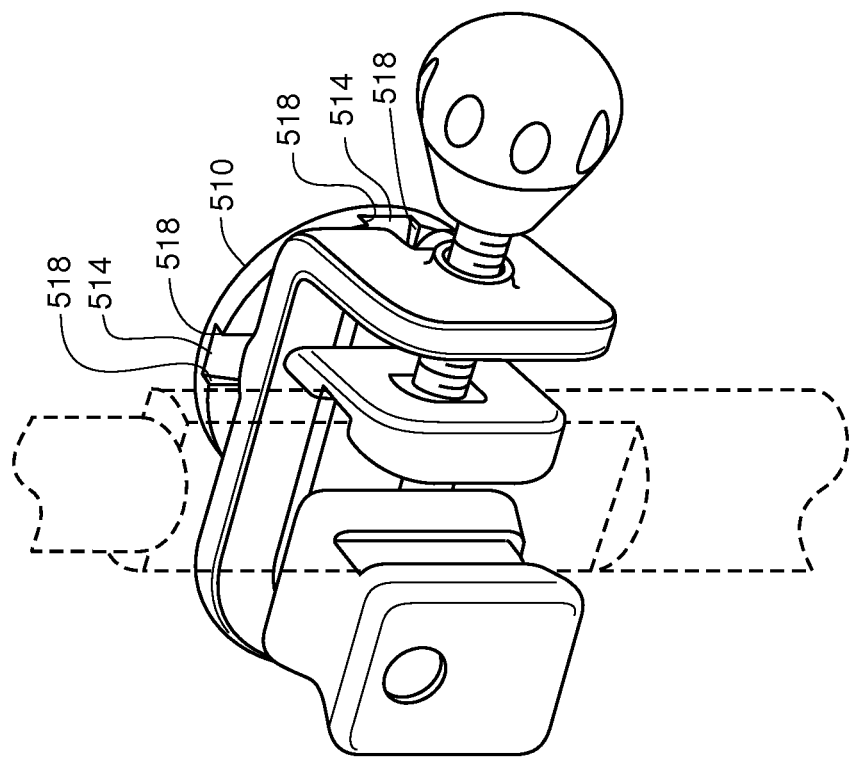
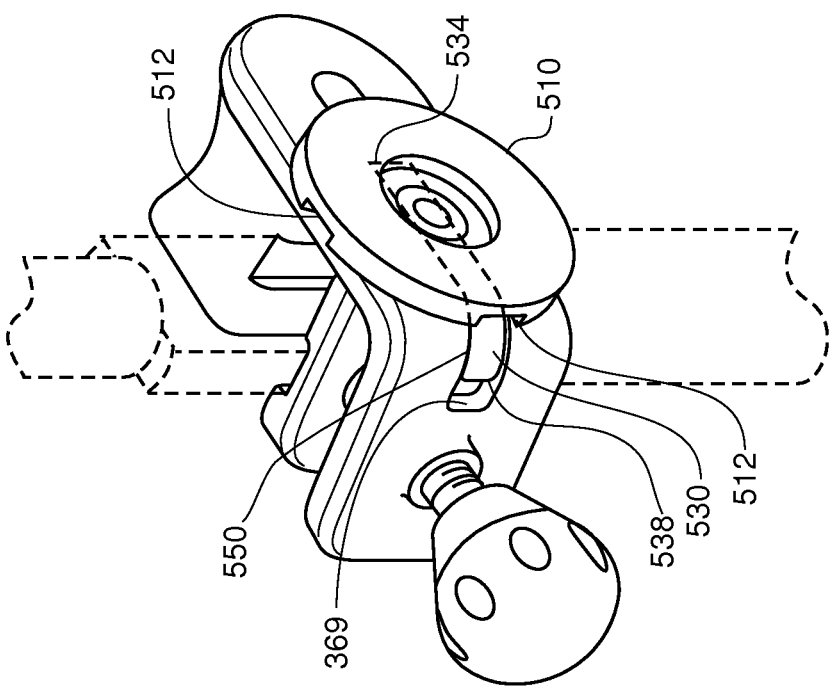

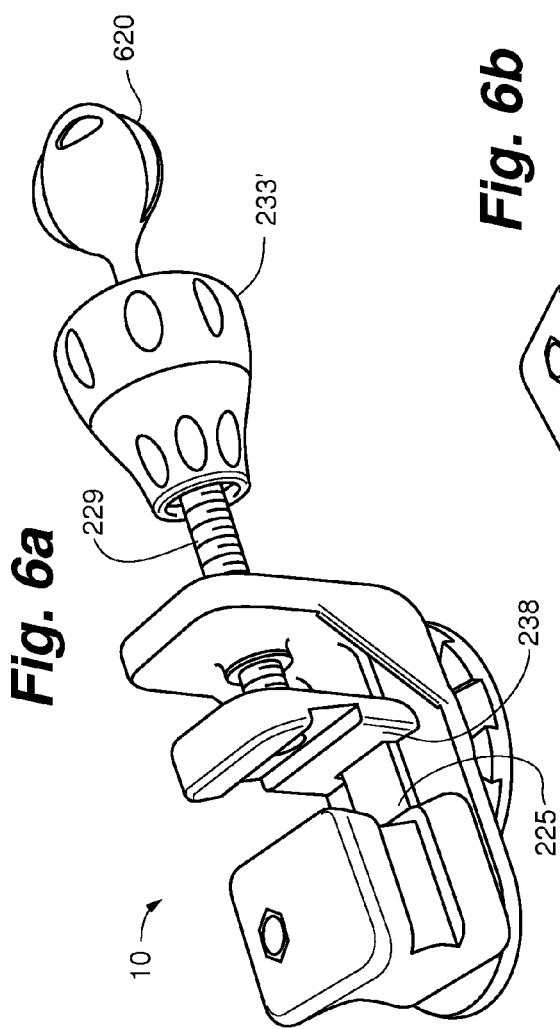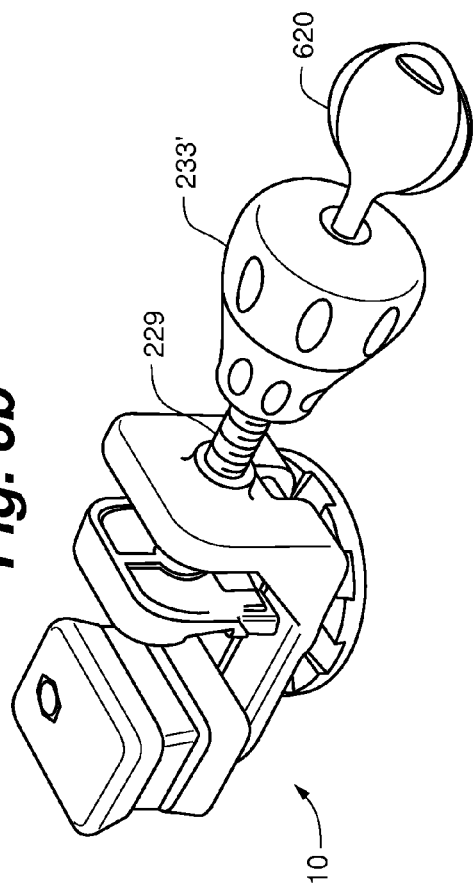

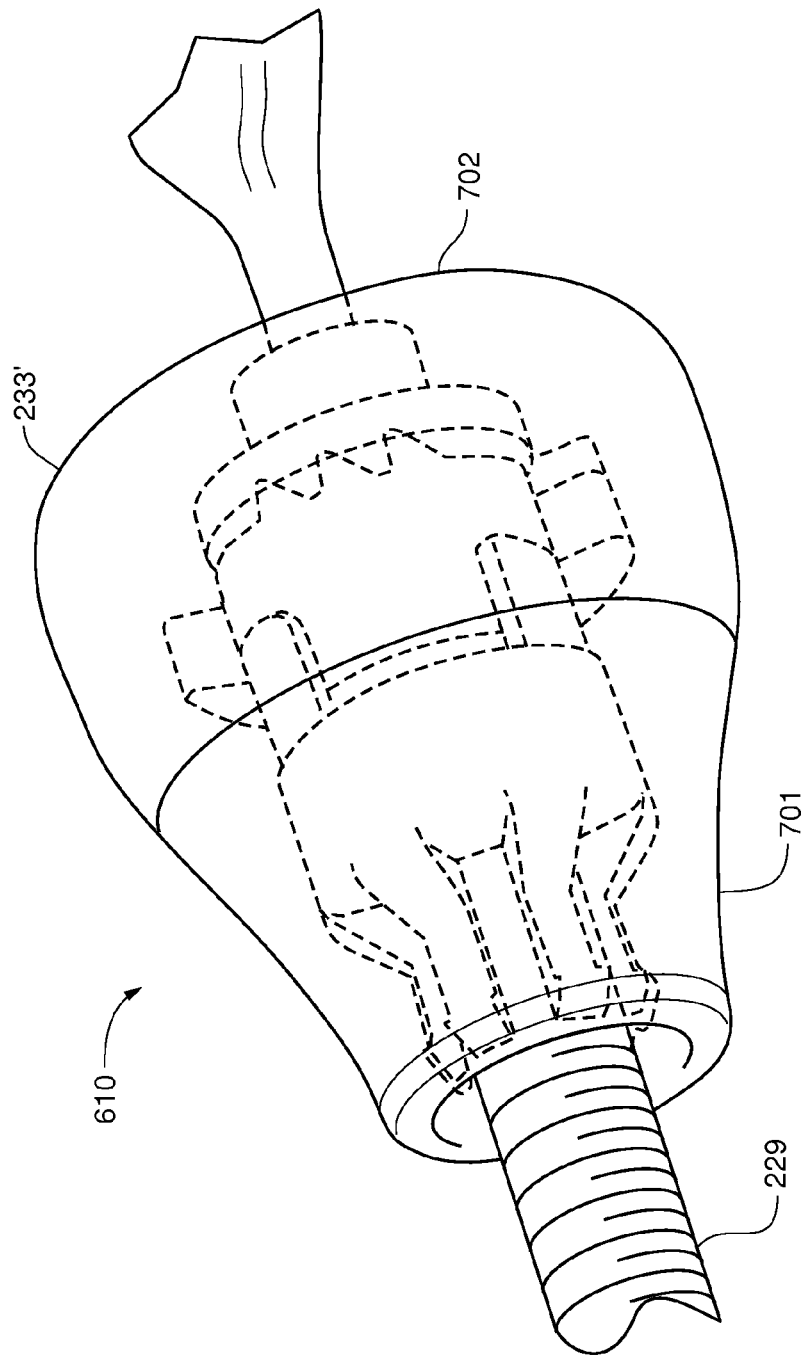

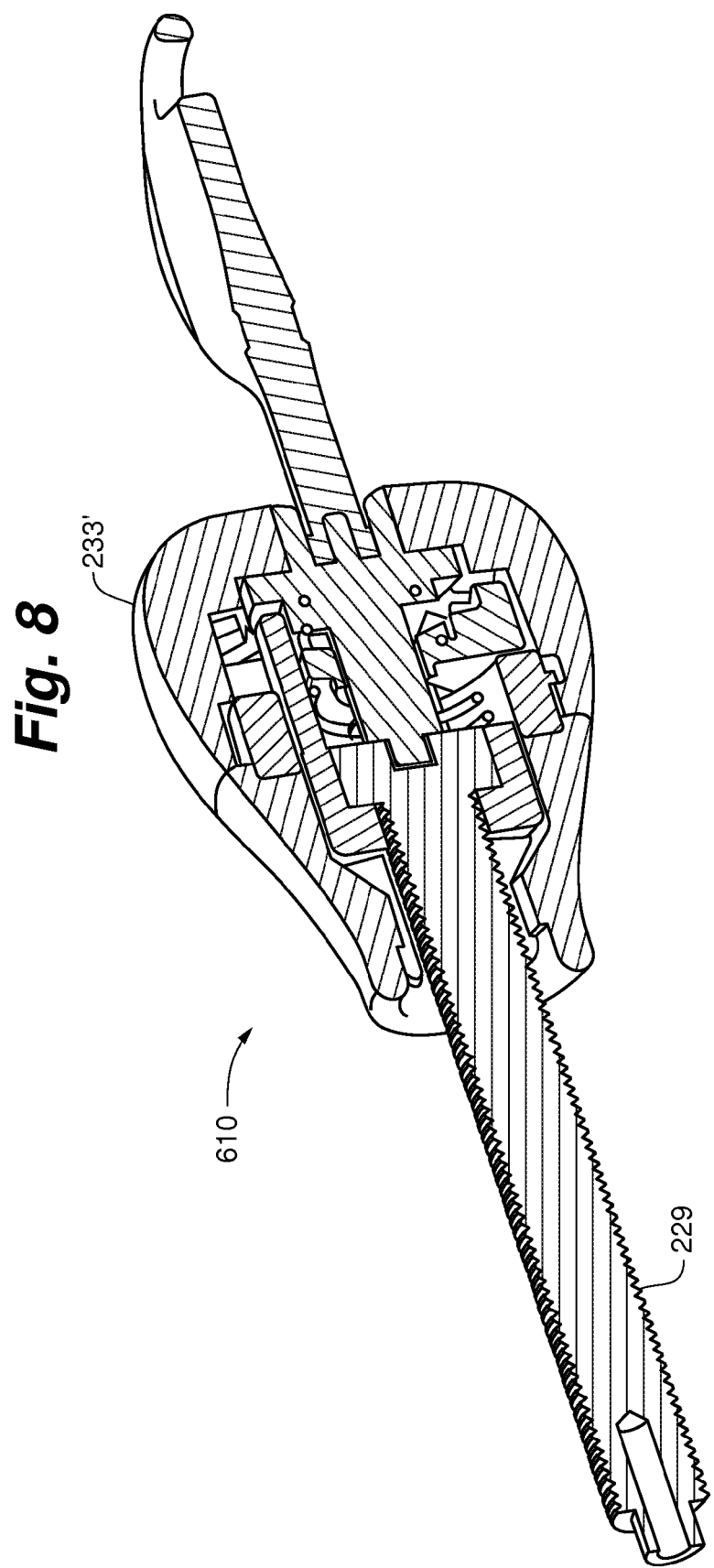

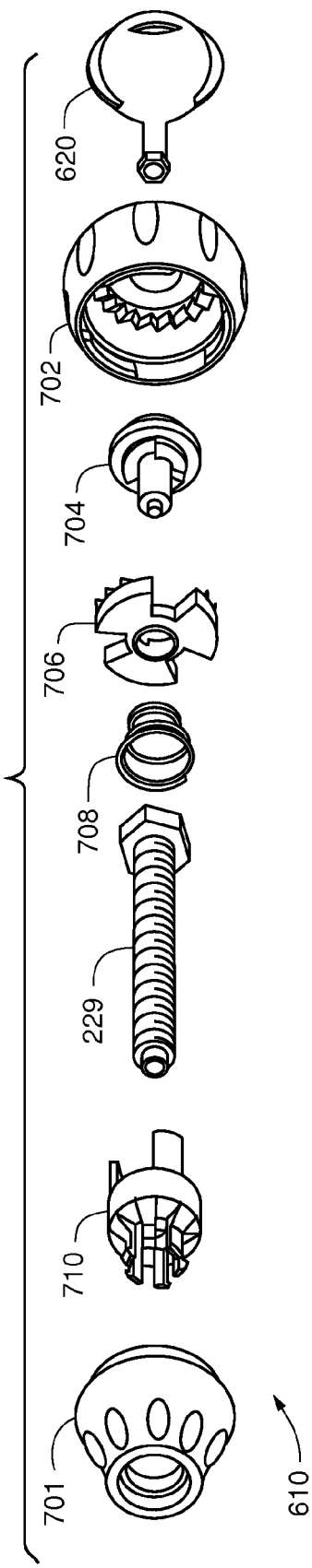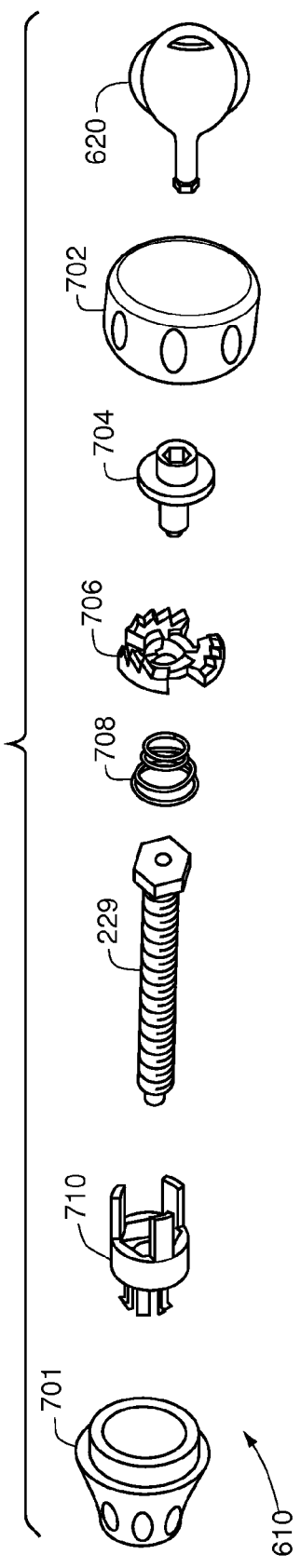

POLE CLAMP

RELATED APPLICATION

This application claims the benefit of U.S. Provisional Patent Application No. 61/927,252 filed Jan. 14, 2014, which is incorporated herein by reference in its entirety.

TECHNICAL FIELD

Subject matter hereof relates generally to clamps, and more particularly, to clamps for securing an operably coupled medical device to a pole.

BACKGROUND

In a hospital or clinic, medical devices are often attached to a clamp which is clamped or secured to a pole located in a room where patients receive diagnostic care and/or treatment. One or more devices can be mounted by clamps on the same pole at the same time. When one of the medical devices is needed to care for a patient in a different area within the hospital or clinic, that device's clamp is unclamped or released from the pole and the device and clamp are relocated to a different pole in the different area. At other times, medical devices may also be dismounted from a pole and remounted to the same pole when the caregiver wishes to change the elevation of the medical device; for example, to better accommodate the particular caregiver's physical stature.

The cross-sectional profile of hospital or clinic poles can vary according to the particular pole model. See, for example, "I.V. POLE STANDS AND TOOL-FREE ACCESSORIES" by MEDLINE, ©2010, which shows several example I.V. pole stands and accessories available from MEDLINE INDUSTRIES, INC. Common cross-sectional shapes include round and rectangular, though other shapes are also possible. The cross-sectional areas of a given shape may also differ from one pole to another. For example, one circular cylindrical pole may have a larger diameter than another circular cylindrical pole. The cross-sectional area for a given pole can also vary, such as when the pole is a telescoping model, in which case an upper portion of the pole can be of a smaller diameter than a lower portion of the pole. It is also possible for the cross-sectional shape to vary within a given pole. For example, such poles can be round in one region and rectangular in another.

Conventional medical device pole clamps typically have a fixed backstop opposite a push plate that is connected to a threaded rod having a turn knob at an opposite end. Hence, when a medical device is dismounted from one circular cross-section pole and moved to another circular cross-section pole, or is repositioned higher or lower on a telescoping circular cross-section pole, the medical professional or other staff member using the pole clamp must spend extra time turning the knob to advance or retract the push plate to fit the new pole circumference. Furthermore, when a medical device is dismounted from a circular cross-section pole and is remounted to a rectangular cross-section pole, the pole clamp may need to be detached from the medical device and a different, more suitable pole clamp attached to the medical device before the medical device is remounted to the new pole.

Therefore, there is a need for a medical device pole clamp that is easily releasable and readily and efficiently adapts to multiple pole cross-sections, including multiple circular cross-sections and varied rectangular (and other shaped) cross-sections.

SUMMARY

Embodiments described or otherwise contemplated herein substantially meet the aforementioned needs. Embodiments comprise a pole clamp that can be attached to, or formed integrally as part of, medical devices for mounting medical devices to poles in hospitals and clinics. In embodiments, medical devices can include infusion pumps such large volume, patient-controlled analgesia (PCA) pumps, elastomeric pumps, syringe pumps, enteral pumps, and/or insulin pumps, patient monitors, and the like. Embodiments of a pole clamp can be readily clamped or secured to the aforementioned poles. The terms "clamped" and "secured" are used interchangeably throughout this specification, as are "unclamped" and "released."

In an embodiment, a pole clamp for mounting a medical device to a pole comprises a main body, including (i) a first portion including a threaded hole therethrough, (ii) a second portion that is disposed at an angle relative to the first portion, and (iii) a pivot post disposed in the second portion; a threaded adjustment rod that is rotatably disposed in and through the threaded hole of the first portion, the threaded adjustment rod having a knob at a first end thereof and a push plate at a second end thereof; and a rotatable stop block having a plurality of faces and being rotatably coupled to the pivot post, the rotatable stop block being rotatable to a plurality of positions to align a selected one of the plurality of faces opposite the push plate.

In an embodiment, a pole clamp comprises a main body. The main body includes a first portion with a threaded hole therethrough and a second portion that is disposed at an angle relative to the first portion. The angle between the first portion and second portion may be acute, perpendicular, or obtuse. In some embodiments, obtuse is preferable for ease of manufacture, cleaning, and/or to avoid creating a region of engineering stress concentration when engaged to a pole.

In an embodiment, the second portion of the main body of the pole clamp comprises a pivot post disposed thereon.

In an embodiment, a threaded adjustment rod is rotatably disposed in and through the threaded hole of the first portion of the main body of the pole clamp. In an embodiment, the threaded adjustment rod has a knob at a first end of the rod and a push plate at a second end of the rod.

In some embodiments, the knob is permanently and fixedly secured to the threaded adjustment rod. In other embodiments, the knob comprises a lock mechanism that, in a first orientation, fixedly secures the knob to the threaded adjustment rod, and in a second orientation, allows the knob to be rotated without a resulting rotation of the threaded adjustment rod.

According to an embodiment, a pole clamp comprises a rotatable stop block mounted on the main body. In an embodiment, the rotatable stop block has a plurality of faces. The rotatable stop block can be rotatably coupled the second portion of the main body by a pivot post. In other embodiments, other coupling mechanisms are possible, such as rotating fasteners or any other suitable securing mechanism. The rotatable stop block is rotatable to a plurality of positions to align with one of the plurality of faces opposite the push plate. In an embodiment, the plurality of faces of the rotatable stop block are contoured to correspond to one of a plurality of pole diameters and contours that results from different pole cross-sectional shapes.

In some embodiments, a medical device is coupled directly to the second portion of the main body of the pole clamp. In other embodiments, a hub is rotatably mounted to the second portion of the main body of the pole clamp and a medical device is mounted to the hub.

In embodiments, the hub comprises a plurality of radially projecting slots. The radially projecting slots are each comprised of a base and an opposing sidewall. The radially projecting slots form a plurality of locking position for mating with a leaf spring. In an embodiment, the leaf spring has at least one end. A first end is mounted to the second portion of the main body of the pole clamp in between the second portion of the main body of the pole clamp and the hub. A second end of the leaf spring projects radially outward from the axis of rotation of the hub and comprises a tab area configured to be accessed by a medical professional or other staff member. In embodiments, the medical professional or other staff member can access the tab area by a finger or tool. When the leaf spring is in a relaxed position, it rests in a mating slot of the hub and prevents the hub from rotating relative to the second portion of the main body of the pole clamp. When the tab of the leaf spring is pulled toward the second portion of the main body of the pole clamp, the leaf spring is pulled away from the slot in the hub that it was occupying. The hub may then be rotated until another slot is aligned with the leaf spring. The medical professional or other staff member can then release the tab of the leaf spring and lock the hub into a new rotational position.

In a feature and advantage of embodiments, medical professionals or other staff members can save time by utilizing the rotatable stop block mounted on the main body. The rotatable stop block is rotatable relative to its centerline so that when the new pole mounting location has a different cross-sectional area and/or shape than the previous pole mounting location, the number of pole clamp threaded rod rotations needed to mount the clamp to the new pole mounting location is approximately the same number of pole clamp threaded rod rotations as was required to remove the clamp from the previous pole mounting location. This is particularly useful when the hospital or clinic uses one of the common, somewhat standard pole models, such as ¾ inch diameter round, 1⅛ inch diameter round, 1¼ inch diameter round, or 25 millimeter by 10 millimeter European rectangular bar.

In a feature and advantage of embodiments, a pole clamp provider can offer a single pole clamp model to a given hospital or clinic that has standardized internally on pole models different from one or more other hospitals or clinics.

The above summary is not intended to describe each illustrated embodiment or every implementation of the subject matter hereof. The figures and the detailed description that follow more particularly exemplify these embodiments.

BRIEF DESCRIPTION OF THE DRAWINGS

Subject matter hereof may be more completely understood in consideration of the following detailed description of various embodiments in connection with the accompanying figures, in which:

FIGS. 5a and 5b are perspective views of a pole with a pole clamp clamped thereto, the pole clamp including an optional hub, according to embodiments.

FIGS. 6a and 6b are perspective views of a pole clamp including an optional hub and an optional locking mechanism, according to embodiments.

FIG. 7 is a perspective view of a knob containing an optional lock mechanism of a pole clamp, wherein the surface of the knob appears translucent such that the lock assembly contained therein is illustrated, according to an embodiment.

FIG. 8 is a cross-sectional view of the perspective view of FIG. 7 of the optional lock mechanism of a pole clamp, according to an embodiment.

FIGS. 9a and 9b are exploded perspective views of the assembly of the optional lock mechanism shown within the knob in FIGS. 7 and 8, according to an embodiment.

Figure 1:
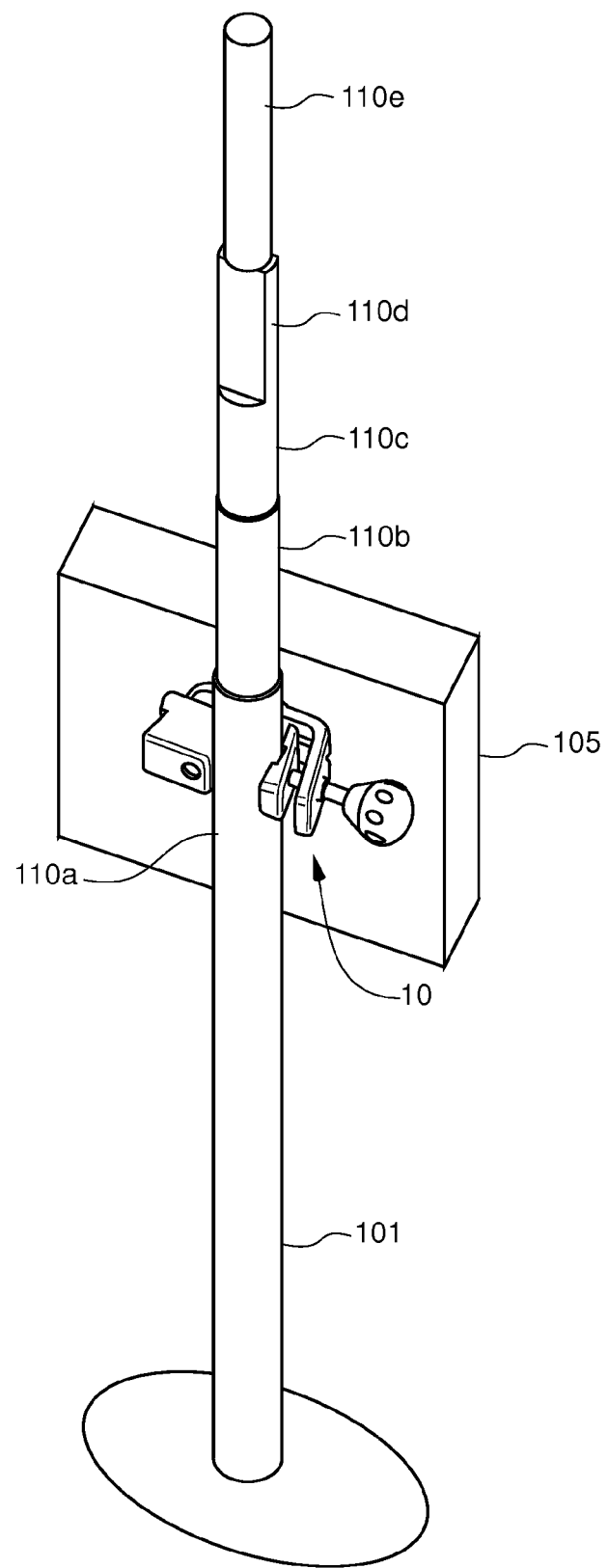
FIG. 1 is a perspective view of a pole clamp, according to an embodiment.

While embodiments are amenable to various modifications and alternative forms, specifics thereof have been shown by way of example in the drawings and will be described in detail. It should be understood, however, that the intention is not to limit subject matter hereof to the particular embodiments described. On the contrary, the intention is to cover all modifications, equivalents, and alternatives falling within the spirit and scope of subject matter hereof in accordance with the appended claims.

DETAILED DESCRIPTION

Referring to FIG. 1, a pole 101 can be located in a hospital, clinic environment. In other embodiments, pole 101 can be located in an equivalent at-home, mobile, or other environment. A medical device 105 is operably coupled to a pole clamp 10. Medical device 105 can be operably coupled to pole clamp 10 by a fastener, such as a bolt or screw, by forming or welding medical device 105 and pole clamp 10 to each other, or by any other suitable attachment known to those skilled in the art.

As depicted in FIG. 1, pole clamp 10 is clamped to pole 101 to mount medical device 105 to pole 101. Pole 101 can have more than one cross-sectional area and/or shape at any given region. For example, pole region 110a can have a larger circumference than pole region 110b, which in turn can have a larger circumference than pole region 110c, which can have a larger circumference than pole region 110e. A suitable pole can also comprise one or more regions with rectangular cross-sections, such as region 110d. Alternatively, a suitable pole can have a uniform cross-sectional shape throughout its entire length.

Figure 2:
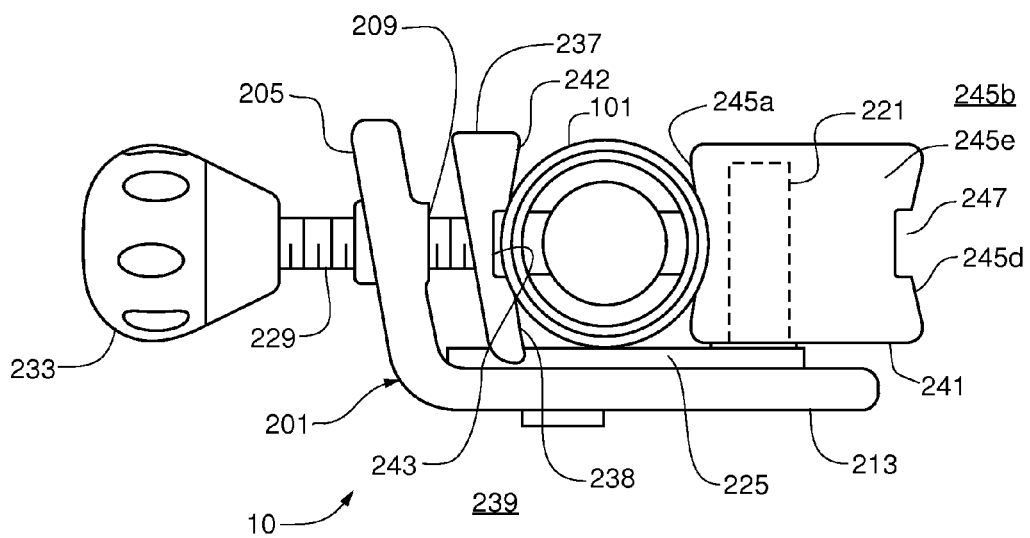
FIG. 2 is a top view of a pole with four different circular cross-sectional diameter regions and one rectangular cross-sectional region with a pole clamp clamped to a region of the pole having the largest circular cross-sectional diameter, according to an embodiment.

Referring to FIG. 2, pole clamp 10 comprises a main body 201. In an embodiment, main body 201 includes a first portion 205 with a threaded aperture 209 therethrough and a second portion 213 that is disposed at an angle relative to first portion 205. In an embodiment, second portion 213 comprises a pivot post 221 disposed thereon. Pivot post 221 is described further below. In some embodiments, the second portion 213 of the main body 201 can optionally include a guiderail 225. Guiderail 225 can be utilized in embodiments to guide one or more portions of pole 101 into engagement with one or more components of pole clamp 10.

Pole clamp 10 further comprises a threaded adjustment rod 229 that is rotatably disposed in and through threaded aperture 209 of the first portion 205 of the main body 201 of the pole clamp 10. The threads of threaded adjustment rod 229 can be larger or smaller than those depicted in FIG. 2, as appropriate for the clamping application. Threaded adjustment rod 229 comprises a knob 233 at a first end of the adjustment rod 229 and a push plate 237 at a second end of the adjustment rod 229. Knob 233 is depicted in FIG. 2 as oblong, but can be any suitable shape configured to engage with a hand or finger of a medical professional or other staff member, or engagement tool utilized by a medical professional or other staff member.

In an embodiment, push plate 237 can optionally have a dovetail contour along its surface that is disposed towards the second portion 213 of the main body 201 to contact with optional guiderail 225 to prevent rotation of push plate 237 when knob 233 is turned.

Pole clamp 10 further comprises a rotatable stop block 241. Rotatable stop block 241 is rotatable about pivot post 221 to a plurality of positions to align rotatable stop block 241 opposite push plate 237 for clamping pole clamp 10 to pole 101. Rotatable stop block 241 can be secured to pivot post 221 by a fastener, such as a bolt or screw, by forming or welding a flange on the end of pivot post 221, or by other suitable attachment known to those skilled in the art, opposite the end of pivot post 221 that is disposed opposite the end of pivot post 221 that is coupled to second portion 213. As illustrated in FIG. 2, pivot post 221 is shown in dashed line within rotatable stop block 241 to depict the aforementioned rotational engagement. In embodiments, pivot post 221 can be larger or smaller than depicted, according to the clamping application and/or size of rotatable stop block 241 or main body 201. In embodiments, pivot post 221 can comprise shapes other than the post depicted.

In an embodiment, rotatable stop block 241 comprises a plurality of faces, sides or surfaces (generally, faces). For example, referring to FIGS. 1 and 2, face 245a is shown contacting pole region 110a. Rotatable stop block 241 in FIG. 2 further comprises a face 245b for contacting pole region 110b, a face 245d for contacting pole region 110d, and a face 245e for contacting pole region 110e. In embodiments, the contour of each face of rotatable stop block 241 is tailored to mate with a given diameter or shape on pole 101. In embodiments, for example, stop block faces configured to contact circular cross-sectional pole regions are concave. In embodiments, stop block faces configured to contact rectangular cross-sectional pole regions comprise a groove 247. Stop block faces can be configured with both a concave surface and a groove, allowing a stop block face to mate with more than one type of pole region. For example, if a stop block has four faces and each face has both a concave portion and a groove portion on its face, the stop block can mate with eight different pole regions. In embodiments, a stop block face can comprise multiple contacting portions, such as a concave portion that further includes a grooved portion within an apex of the curve. In embodiments, rotatable stop block 241 comprises a generic face or face portion that readily adapts to multiple types of pole regions.

The contour of push plate face 238 is configured to accommodate the surface of multiple pole regions. In embodiments in which push plate 237 is configured to mate with a circular cross-section region of pole 101, push plate face 238 comprises a concave surface 242. In embodiments in which push plate 237 is designed to mate with a rectangular cross-section region of pole 101, push plate face 238 comprises a groove 243 in addition to concave surface 242. In embodiments, push plate face 238 comprises a concave surface 242 (not shown) without a groove 243. In other embodiments, push plate face 238 comprises a groove 243 without a concave surface 242. In other embodiments, push plate face 238 comprises a generic face or face portion adapted to engaged multiple types of pole regions.

Figure 3:
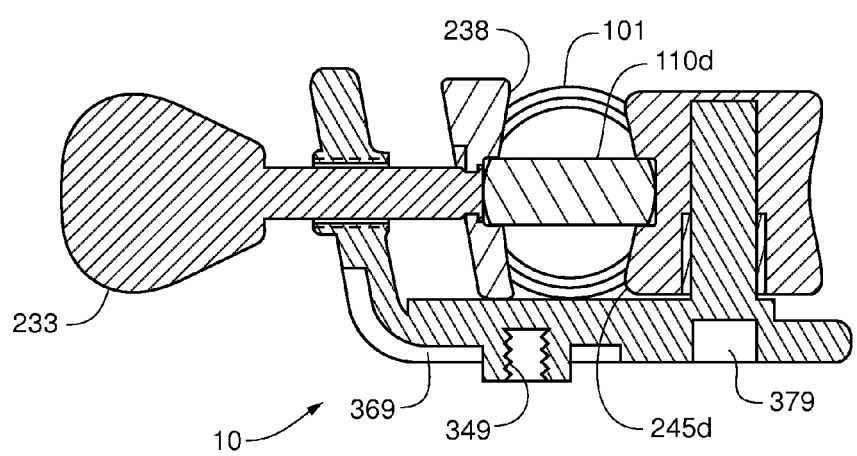
FIG. 3 is a top cross-sectional view of a pole with a pole clamp clamped to a region of the pole having a rectangular cross-sectional region, according to an embodiment.

Referring to FIG. 3, pole clamp 10 is engaged with rectangular cross-sectional region 110d of pole 101. Stop block face 245d is shown mating with rectangular cross-sectional region 110d. Push plate face 238 is shown mating with region 100d of pole 101.

In some embodiments, second portion 213 of main body 201 further comprises threads 349 for connecting a medical device 105 to the second portion 213 by a suitable connection means, such as a bolt or screw.

In other embodiments, second portion 213 of the main body 201 of the pole clamp 10 can comprise a void 369 that can optionally continue around the outer bend or corner of main body 201 and into the first portion 205 of the main body 205 of the pole clamp 10. As will be described, void 369 can comprise other shapes or configurations than those depicted.

In embodiments, second portion 213 of the main body 201 of the pole clamp 10 comprises a clearance aperture 379 to receive a fastener (not shown) in order to secure stop block 241 onto pivot post 221.

Figure 4B:
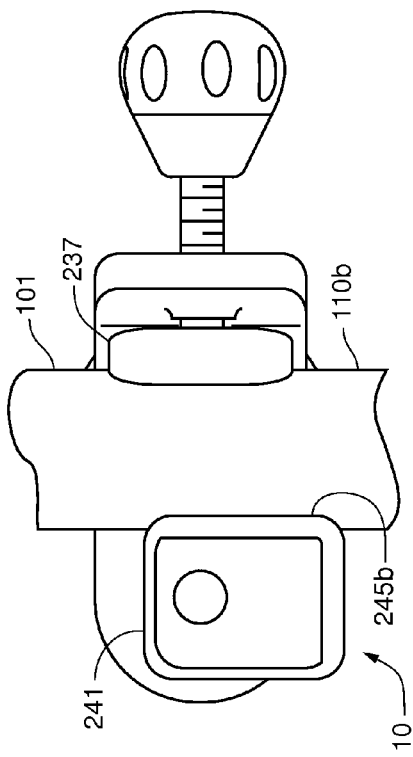
FIGS. 4a, 4b, 4c, and 4d are side views of pole regions having embodiments of a pole clamp clamped thereto.
Figure 4D:
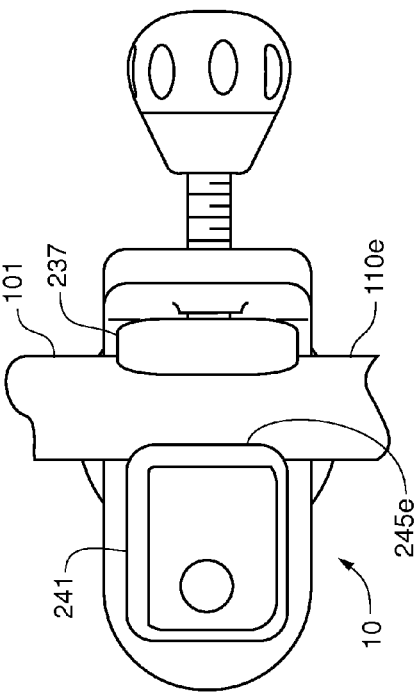
Figure 4A:
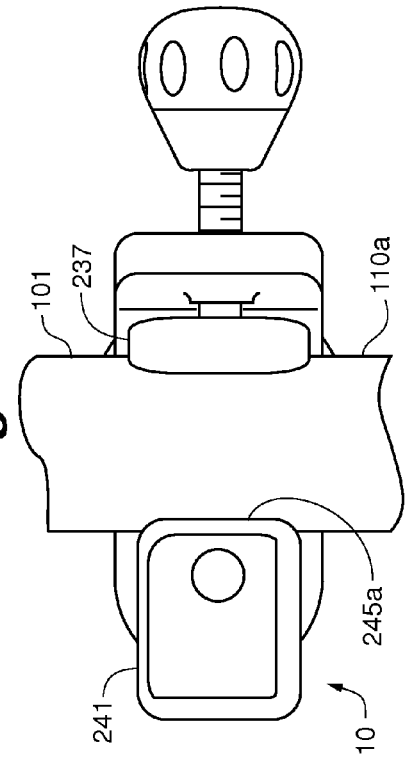

Referring to FIG. 4a, pole clamp 10 is clamped to circular cross-sectional pole region 110a of pole 101. Push plate 237 and face 245a of stop block 241 are each engaged to respective portions of circular cross-sectional pole region 110a.

Referring to FIG. 4b, pole clamp 10 is clamped to circular cross-sectional pole region 110b of pole 101. Push plate 237 and face 245b of stop block 241 are each engaged to respective portions of circular cross-sectional pole region 110b.

Figure 4C:
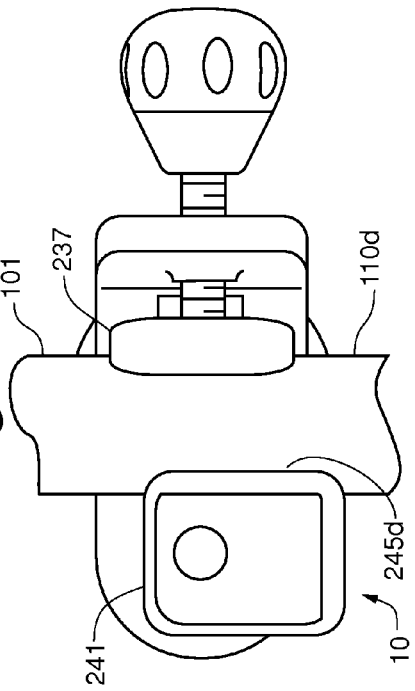

Referring to FIG. 4c, pole clamp 10 is clamped to rectangular cross-sectional pole region 110d of pole 101. Groove 243 of push plate 237 and grove 247 of face 245d of stop block 241 are both engaged to respective portions of rectangular cross-sectional pole region 110d.

Referring to FIG. 4d, pole clamp 10 is clamped to circular cross-sectional pole region 110e of pole 101. Push plate 237 and face 245e of stop block 241 are each engaged to respective portions of circular cross-sectional pole region 110e.

In operation, pole claim 10 can be disengaged or released from pole 101 by turning knob 233 until push plate 237 has backed away from pole 101 a sufficient distance to allow dismounting of pole clamp 10 from pole 101. The threaded engagement of threaded adjustment rod 229 through aperture 209 allows push plate 237 to be backed away from pole 101. Pole clamp 10 can then be moved to a pole or pole region with a different cross-sectional area or cross-sectional shape. In embodiments, the threaded engagement of threaded adjustment rod 229 through aperture 209 allows push plate 237 to be advanced towards pole 101.

For example, a medical professional or other staff member moving pole clamp 10 from pole region 110a to pole region 110b, would first rotate stop block 241 such that face 245b faces pole region 110b instead of face 245a. The number of pole clamp threaded rod 229 rotations needed to mount pole clamp 10 to pole region 110b will be approximately the same number of pole clamp threaded rod 229 rotations as was required to remove pole claim 10 from pole region 110a.

In another example, a medical professional or other staff member moving pole clamp 10 from a first pole having a shape and cross-sectional dimensions similar to that of pole region 110e to a second pole having a shape and cross-sectional dimensions similar to that of pole region 110d, would rotate stop block 241 such that face 245d faces the second pole instead of face 245e. In an embodiment, the number of pole clamp threaded rod 229 rotations needed to mount pole clamp 10 to the second pole is approximately the same number of pole clamp threaded rod 229 rotations as was required to remove pole claim 10 from the first pole. In some embodiments, the number of pole clamp threaded rod 229 rotations can be approximately equal, especially in the case where the pole clamp is removed from a pole region with a circular cross-sectional area and reclamped to a pole region with a rectangular cross-sectional area, and vice versa, as the depth of push plate grove 243 may be configured to any suitable depth.

In some embodiments, referring again to FIG. 1, medical device 105 can be coupled directly to second portion 213. However, in other embodiments, referring to FIGS. 5*a* and 5*b*, an optional hub 510 is rotatably mounted to second portion 213 such that medical device 105 (not shown) can be coupled to hub 510 instead of second portion 213. The coupling of medical device 105 to hub 510 can be by a fastener, such as a bolt or screw, by forming or welding medical device 105 and pole clamp 10 to each other, or by other suitable attachment known to those skilled in the art.

In an embodiment, hub 510 comprises one or more radially projecting slots 512. In an embodiment, slots 512 have a base 514 and opposing sidewalls 518. The slots 512 form a plurality of locking positions for mating with a leaf spring 530. In an embodiment, leaf spring 530 comprises one or more ends. A first end 534 is operably coupled to second portion 213 of main body 201 in between second portion 213 and hub 510. In embodiments, first end 534 can be operably coupled to second portion 213 by a bolt, a screw, be formed integral to each other, welding, or any other suitable coupling known to those skilled in the art.

A second end 538 of leaf spring 530 projects radially outward from the axis of rotation of hub 510 and comprises a tab area 550 that may be accessed by a finger or tool. When leaf spring 530 is in a relaxed position, leaf spring 530 rests in a mating slot 512 of hub 510 and prevents hub 510 from rotating relative to second portion 213. When tab 550 of leaf spring 530 is pulled toward second portion 213, leaf spring 530 is pulled away from slot 512 in hub 510 that it was occupying and into void 369. Hub 510 can then be rotated until another slot 512 is aligned with leaf spring 530. The medical professional or other staff member can then release tab 550 of leaf spring 530. Once tab 550 is released, leaf spring 530 leaves the temporary position in void 369 and returns to rest in the newly aligned slot 512 and secures hub 510 into a new rotational position.

In an embodiment, a medical professional or other staff member can utilize hub 510 and its components as described above to release a medical device from a horizontal mounting position and reorient and reattach the medical device in a vertical mounting position. In other embodiments, the medical professional or other staff member can utilize hub 510 to release the medical device from a vertical mounting position and reattach the medical device in a horizontal mounting position. In embodiments, the aforementioned releasing and reattaching can be on the same pole; for example, moving from a horizontal mounting position on a vertical pole to a vertical mounting position on the same vertical pole. In other embodiments, the aforementioned releasing and reattaching can be on different poles; for example, moving from a horizontal mounting position on a horizontal pole to a vertical mounting position on a vertical pole.

In embodiments, knob 233 is permanently fixedly coupled to threaded adjustment rod 229, as illustrated in FIG. 3. In other embodiments, for example, referring to knob 233' in FIGS. 6*a* and 6*b*, a knob 233' can comprise a lock mechanism that, in a first orientation, fixedly secures knob 233' to a threaded adjustment rod and, in a second orientation, allows the knob to be rotated without a resulting rotation of the threaded adjustment rod.

In an embodiment, referring again to FIGS. 6*a* and 6*b*, as well as FIGS. 7, 8, 9*a*, and 9*b*, knob 233' comprises a lock mechanism 610. In an embodiment, lock mechanism comprises a key 620. When key 620 is used to operate lock mechanism 610 to a first orientation, lock mechanism 610 fixedly secures knob 233' to threaded adjustment rod 229. When key 620 is used to operate lock mechanism 610 in a second orientation, lock mechanism 610 allows knob 233' to be rotated by a medical professional or other staff member without a resulting rotation of threaded adjustment rod 229. Such second orientation of lock mechanism 610 prevents removal of pole clamp 10 from a pole by unauthorized personnel, or even thieves, who do not possess key 620.

Referring specifically to FIGS. 7, 8, 9*a*, and 9*b*, an embodiment of locking mechanism 610 within knob 233' is illustrated. For ease of assembly, knob 233' can comprise more than one housing portion. A first housing portion 701 can be disposed about the circumference of threaded adjust rod 229. A second housing portion 702 can be matingly attached to first housing portion 701 to complete the housing assembly formed to create the exterior of knob 233'. In other embodiments, knob 233' housing can comprise a single housing portion. In the embodiment shown, an interior of second housing portion 702 comprises a repeating sawtooth pattern, the pattern repeating about a circular path, to form a portion of lock mechanism 610.

Referring to FIGS. 8, 9*a*, and 9*b*, knob 233' and lock mechanism 610 further comprises key receiver 704, toothed adapter 706, spring 708, threaded adjustment rod 229, and first housing adapter 710.

Key receiver 704 is configured to receive key 620. As such, a portion proximate second housing portion 702 can be received within second housing portion 702 and configured such that the portion proximate second housing portion 702 comprises a shape unique to key 620. As depicted in the embodiment of FIGS. 9*a* and 9*b*, both key 620 and key receiver 704 comprise a hexagonal shape. Other shapes and configurations are, of course, possible. The portion of key receiver 704 proximate second housing portion 702 is sized such that it makes frictional engagement with key 620. Key receiver 704 further comprises a projection configured to contact threaded adjustment rod 229. In embodiments, key receiver 704 further comprises a series of projections that interface to toothed adapter 706.

Toothed adapter 706 is configured to receive the projection of key receiver 704 and pass the projection therethrough. Toothed adapter 706 further comprises a series of sawtooth projections configured to engage with the corresponding repeating sawtooth pattern of second housing portion 702. In an embodiment, toothed adapter 706 further comprises one or more voids that interface with first housing adapter 710.

Spring 708 provides springing engagement between threaded adjustment rod 229 and the projection of key receiver 704 further configured to contact threaded adjustment rod 229.

First housing adapter 710 is configured to be received by first housing 701. First housing adapter comprises one or more projections that align with the one or more voids in toothed adapter 706 such that first housing adapter 710 and toothed adapter 706 move together. First housing adapter 710 is further configured to receive threaded adjustment rod 229 therethrough.

Therefore, as described above, when key 620 directs lock mechanism 610 in a first orientation, lock mechanism 610 fixedly secures knob 233' to threaded adjustment rod 229. Particularly, key 620 engages key receiver 704, which interfaces with a non-toothed portion of second housing 702.

Toothed adapter 706 locks its teeth with respective portions of the sawtooth patterned portion of second housing 702. The voids of toothed adapter 706 engage the projections of first housing adapter 710. In such a configuration, any turn of knob 233' engages, via housings 701 and 702 to key receiver 704 projection, threaded adjustment rod 229.

Likewise, key 620 can direct lock mechanism 610 in a second orientation, such that lock mechanism 610 allows knob 233' to be rotated without a resulting rotation of threaded adjustment rod 229. Particularly, key 620 engages key receiver 704 such that the interface between toothed adapter 706 and the respective portions of the sawtooth patterned portion of second housing 702 are disengaged (see, for example, FIG. 7), and knob 233' freely rotates without (additional or any, depending on the state of the previous contact) engagement of key receiver 704 projection to threaded adjustment rod 229.

Various embodiments of systems, devices, and methods have been described herein. These embodiments are given only by way of example and are not intended to limit the scope of subject matter hereof. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized commensurate with the scope of subject matter hereof.

Persons of ordinary skill in the relevant arts will recognize that subject matter hereof may comprise fewer features than illustrated in any individual embodiment described above. The embodiments described herein are not meant to be an exhaustive presentation of the ways in which the various features of subject matter hereof may be combined. Accordingly, the embodiments are not mutually exclusive combinations of features; rather, the subject matter hereof may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims of subject matter hereof, it is expressly intended that the provisions of Section 112, sixth paragraph of 35 U.S.C. are not to be invoked unless the specific terms "means for" or "step for" are recited in a claim.

The invention claimed is:

1. A pole clamp for mounting a medical device to a pole, comprising:
    a main body, including (i) a first portion including a threaded hole therethrough, (ii) a second portion that is disposed at an angle relative to the first portion, and (iii) a pivot post disposed in the second portion;
    a threaded adjustment rod that is rotatably disposed in and through the threaded hole of the first portion, the threaded adjustment rod having a knob at a first end thereof and a push plate at a second end thereof; and
    a rotatable stop block having a plurality of faces and being rotatably coupled to the pivot post, the rotatable stop block being rotatable to a plurality of positions to align a selected one of the plurality of faces opposite the push plate.

2. The pole clamp of claim 1, wherein each of the plurality of faces of the rotatable stop block is contoured to correspond to at least one of a plurality of external pole profiles.

3. The pole clamp of claim 1, wherein the angle between the first and second portions is between about 90 degrees and about 135 degrees.

4. The pole clamp of claim 1, wherein the knob comprises a locking mechanism that in a first orientation fixedly secures the knob to the threaded adjustment rod, and in a second orientation allows the knob to be rotated without a resulting rotation of the threaded adjustment rod.

5. The pole clamp of claim 1, further including a hub coupled to the second portion of the main body.

6. The pole clamp of claim 5, wherein the hub is rotatable.

7. The pole clamp of claim 6, wherein the hub has a plurality of locking positions.

* * * * *